(12) United States Patent
Liang et al.

(10) Patent No.: US 9,364,510 B2
(45) Date of Patent: Jun. 14, 2016

(54) BOTANICAL COMPOSITION AND METHODS OF MANUFACTURE AND USE

(71) Applicant: MarvPhyt Development LLC, Lewes (DE)

(72) Inventors: Xi Juan Liang, Tianjin (CN); Bing Lian Wu, Tianjin (CN)

(73) Assignee: MARVPHYT DEVELOPMENT LLC, Lewes, DE (US)

( * ) Notice: Subject to any disclaimer, the term of this patent is extended or adjusted under 35 U.S.C. 154(b) by 101 days.

(21) Appl. No.: 14/159,969

(22) Filed: Jan. 21, 2014

(65) Prior Publication Data
US 2014/0199421 A1    Jul. 17, 2014

Related U.S. Application Data

(63) Continuation-in-part of application No. PCT/US2011/044488, filed on Jul. 19, 2011.

(51) Int. Cl.
*A61K 36/41* (2006.01)
*A61K 36/42* (2006.01)
*A23L 1/30* (2006.01)

(52) U.S. Cl.
CPC ............... *A61K 36/41* (2013.01); *A23L 1/3002* (2013.01); *A61K 36/42* (2013.01)

(58) Field of Classification Search
CPC ............................. A61K 36/41; A61K 36/42
USPC .................................................. 424/774, 776
See application file for complete search history.

(56) References Cited

U.S. PATENT DOCUMENTS

| 2004/0127395 A1 | 7/2004 | Desai et al. |
| 2005/0090527 A1 | 4/2005 | Anthes et al. |
| 2009/0069343 A1 | 3/2009 | Dunford et al. |

FOREIGN PATENT DOCUMENTS

| ES | 2 104 516 | 10/1997 |
| JP | 2009-149572 | 7/2009 |
| WO | WO 2011/006100 | 1/2011 |

OTHER PUBLICATIONS

Bonina et al. "In-vitro Antioxidant and In-vivo Photoprotective Effect of Three Lyophilized Extracts of Sedum telephium L. Leaves", J. Pharm. Pharmacol. 2000, 52; 1279-1285.*
Fang et al, "Anti-inflammatory and free radical scavenging activities of ethanol of three seeds used as 'Bolengguazi' ", Journal of Ethnopharmacology; 114; (2007); 61-65.*
Altavilla et al. "Anti-inflammatory Effects of the Methanol Extract of Sedum telephium ssp. maximum in Lipopolysaccharide-Stimulated Rat Pertoneal Macrophages", Pharmacology; 2008; 82; 250-256.*
Abstract, Gilchrest BA, et al., "The human sunburn reaction: histologic and biochemical studies" J Am Acad Dermatol. Oct. 1981; 5(4): 411-22 (or vide: http://www.ncbi.nlm.nih.gov/pubmed/7287956).
Abstract, Database WPI, Week 198813, Thomas Scientific, London, GB; AN 1988-086567, XP002658730 (HU T44165 A) (Vadasz P), Feb. 29, 1988.
Article, Sendl et al., "*Anti-Inflammatory and Immunologically active polysaccharides of Sedum telephium*", Photochemistry, Pergamon Press, GB, vol. 34, No. 5, Nov. 1, 1993 (pp. 1357-1362).
Abstract, Shinoda S, et al., "*Histamine enhances UVB-induced IL-6 production by human keratinocytes*" Arch Dermatol Res. Aug. 1998; 290(8): 429-34 (or vide: http://www.ncbi.nlm.nih.gov/pubmed/9763305).
Article, Kang et al., "*Antiproliferative effects of alkaloids from Sedum sarmentosum on murine and human hepatoma cell lines*", Journal of Ethnopharmacology, vol. 70, Jan. 1, 2000, pp. 177-182.
Article, Bonina et al., "*In-vitro antioxidant and in-vivo photoprotective effect of three lyophilized extracts of Sedum telephium L. leaves*", Journal of Pharmacy and Pharmacology, Royal Pharmaceutical Society of Great Britain, vol. 52, No. 10, Oct. 1, 2000, pp. 1279-1285.
Abstract, Yoshida M, et al, "*Histamine is involved in ultraviolet B-induced pigmentation of guinea pig skin*", J Invest Dermatol. Feb. 2002;118(2):255-60 (or see: http://www.ncbi.nlm.nih.gov/pubmed/11841541).
Abstract, Rosenwasser LJ. "*Treatment of allergic rhinitis*" Am J Med. Dec. 16, 2002; 113 Suppl 9A: 17S-24S (Vide: http://www.ncbi.nlm.nih.gov/pubmed?term=12517578).
Abstract, Stulberg DL, et al., "*Common hyperpigmentation disorders in adults: Part II. Melanoma, seborrheic keratoses, acanthosis nigricans, melasma, diabetic dermopathy, tinea versicolor, and postinflammatory hyperpigmentation.*" Am Fam Physician. Nov. 15, 2003; 68(10): 1963-8 (or see: http://www.ncbi.nlm.nih.gov/pubmed/14655805).
Abstract, Kim D.W. et. al., "*Anti-inflammatory activity of Sedum kamtschaticum*", Medicinal & Aromatic Plants Abstract, Scientific Publishers, New Delhi, India, vol. 27, No. 2, Mar. 1, 2005, pp. 409-414.
Abstract, Tomita K, et. al, "Histamine regulates growth of malignant melanoma implants via H2 receptors in mice" Inflammopharmacology. 2005; 13(1-3): 281-9 (or see: http://www.ncbi.nlm.nih.gov/pubmed/16259747).
Abstract, Xu KS, et al., "Changes of mast cells and protease activated receptor-2 in experimental rat liver fibrosis" Zhonghua Gan Zang Bing Za Zhi. Oct. 2006; 14(10): 753-6 (or vide: http://www.ncbi.nlm.nih.gov/pubmed/17064469.
Article, Jung et al., "*Anti-Inflammatory, anti-angiogenic and anti-nociceptive activities of Sedum sarmentosum extract*", Journal of Ethnopharmacology, Elsevier Scientific Publishers Ltd., IE, vol. 116, No. 1, Nov. 21, 2007, pp. 138-143.

(Continued)

*Primary Examiner* — Chris R Tate
*Assistant Examiner* — Deborah Davis
(74) *Attorney, Agent, or Firm* — Brinks Gilson & Lione; G. Peter Nichols

(57) ABSTRACT

A botanical composition and combinations thereof that include a leaf extract of *Hylotelephium spectabile* (Boreau) *H. Ohba* and is useful for treating and/or preventing histamine-mediated conditions or disorders are described. Methods of manufacture and use thereof are also described.

10 Claims, 3 Drawing Sheets

(56) References Cited

OTHER PUBLICATIONS

Abstract, Festa et al., "*Phenolic Glycosides from Cucumis melo var. inodorus Seeds*" International PSE Symposium on Natural Products in Cancer Therapy, Sep. 23-26, 2008, Naples, Italy (10 pages).
Abstract, Jung et al., "*Anti-inflammatory, anti-angiogenic and anti-nociceptive activities of Sedum sarmentosum extract*", Medicinal & Aromatic Plants Abstracts, Scientific Publishers, New Dehli, India, vol. 31, No. 1, Feb. 1, 2009.
Article, De Melo et al., "*Antinociceptive and anti-inflammatory kaempferol glycosides from Sedum dendroideum*", Journal of Ethnopharmacology, Elsevier Scientific Publishers Ltd., IE, vol. 124, No. 2, Jul. 15, 2009, pp. 228-232.
Abstract, Blaya B, et al, "*Histamine and histamine receptor antagonists in cancer biology*", Inflamm Allergy Drug Targets. Jul. 1, 2010;9(3):1 46-57 (or see: http://www.ncbi.nlm.nih.gov/pubmed/20632959).
Abstract, Kim NH, et al, "*Histamine effect on melanocyte proliferation and vitiliginous keratinocyte survival*", Exp Dermatol. Dec. 2010; 19(12):1073-9 (or See: http://www.ncbi.nlm.nih.gov/pubmed/21054556).
Article, Gauglitz et al., Hypertrophic Scarring and Keloids: Pathomechanisms and Current and Emerging Treatment Strategies Mol. Med. Jan.-Feb. 2011; 17(1-2): 113-125 (or vide: http://www.ncbi.nlm.nih.gov/pmc/articles/PMC3022978).
Abstract, Müller K, et al., "*Radiation-induced mast cell mediators differentially modulate chemokine release from dermal fibroblasts*" J Dermatol Sci. Mar. 2011; 61(3): 199-205. Epub Jan. 15, 2011 (or vide: http://www.ncbi.nlm.nih.gov/pubmed/21292447).
Abstract, Lei et al., "*Method for extracting total flavonoids from Hylotelephium purpureum and its application for treating recurrent aphtha, oral ulcer and periodontitis*", XP000002658732, May 25, 2011(3 pages).
PCT/US2011/044488 International Search Report dated Sep. 30, 2011 (5 pages).
Abstract, Veerappan A, et al., "Mast cells: a pivotal role in pulmonary fibrosis" DNA Cell Biol. Apr. 2013; 32(4): 206-18 (or vide: http://www.ncbi.nlm.nih.gov/pubmed/23570576).
Website link to http://en.wikipedia.org/wiki/Dandruff (page last modified Jan. 11, 2014).
Website link to http://en.wikipedia.org/wiki/Allergic_conjunctivitis (page last modified Jan. 13, 2014).
Website link to http://en.wikipedia.org/wiki/Melanoma (page last modified Jan. 18, 2014).
Website link to http://en.wikipedia.org/wiki/Food_allergy (page last modified Jan. 18, 2014).
Website link to photograph of leaf extract Hylotelephium spectabile (Boreau) H.Ohba (a/k/a "Hylotelephium composition"; http://www.zhiwutong.com/dan_tu/70/56014.htm (undated).
Website link to photograph of Cucumis melo L. (a/k/a Melon Pedical Powder); http://www.e2121.com/herb_db/viewherb.php3?viewid=624&setlang (undated).

\* cited by examiner

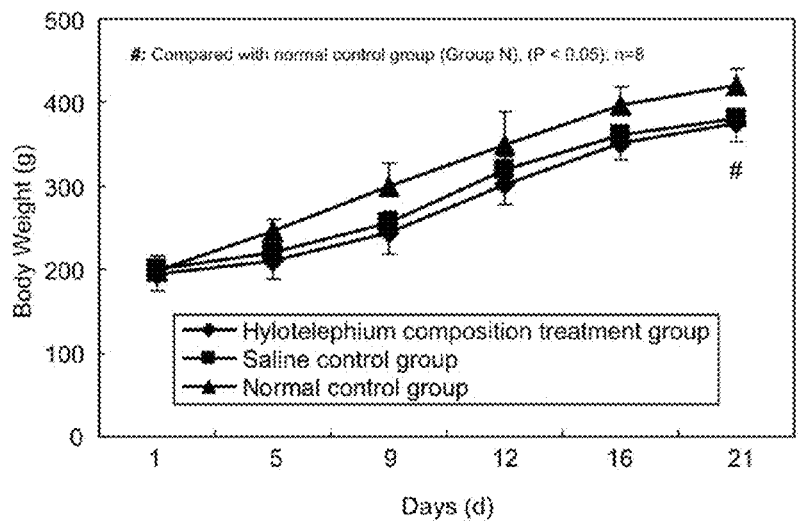
FIG. 1A Changes of body weight of rats
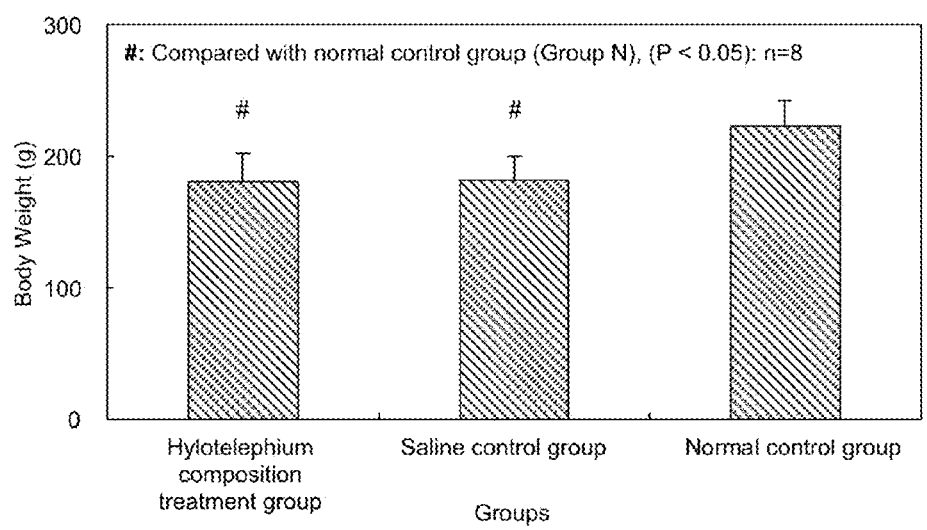
FIG. 1B Changes of body weight of rats

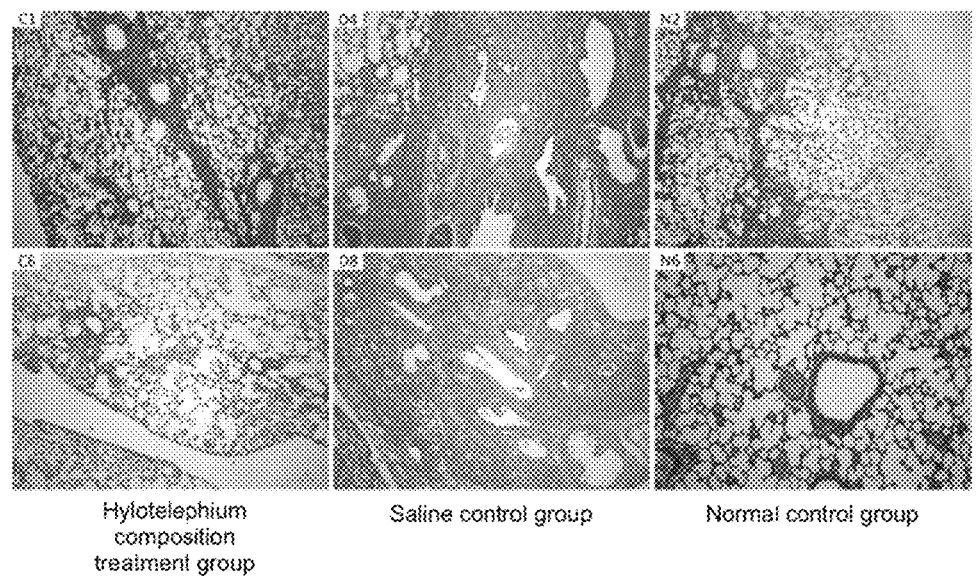
FIG. 2A
Lung tissue profiles of typical rats obtained by the histological examinations
(HE×100)
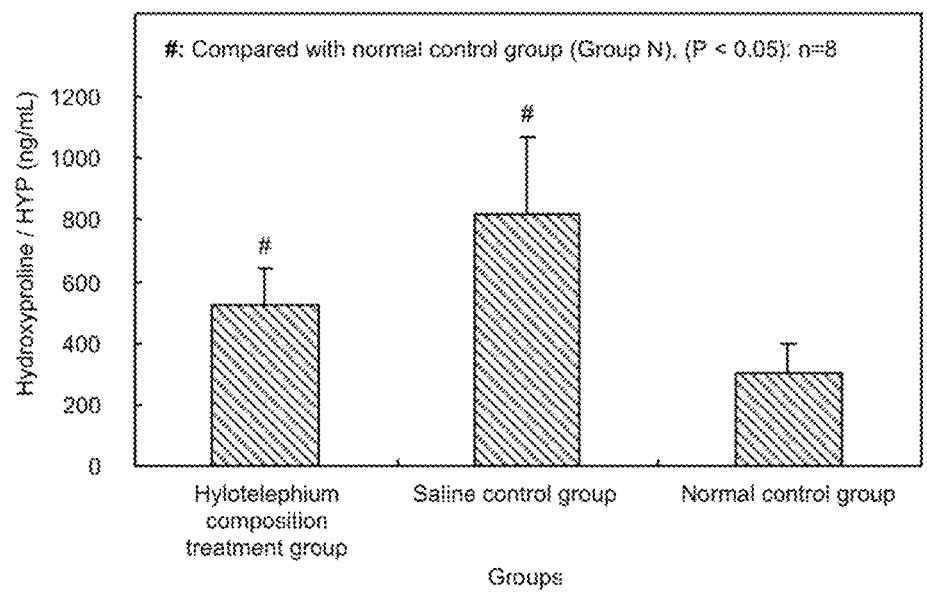
FIG. 2B  Effect of Hylotelephium composition on hydroxyproline content in rat's left lung tissue with fibrosis

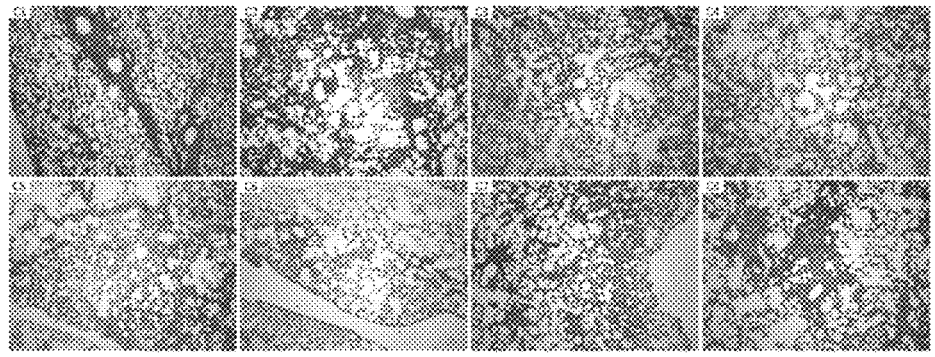

FIG. 3A: Lung tissue profiles of rats from Group C
(Hylotelephium composition treatment group)
with bleomycin-induced pulmonary fibrosis (HE×100)

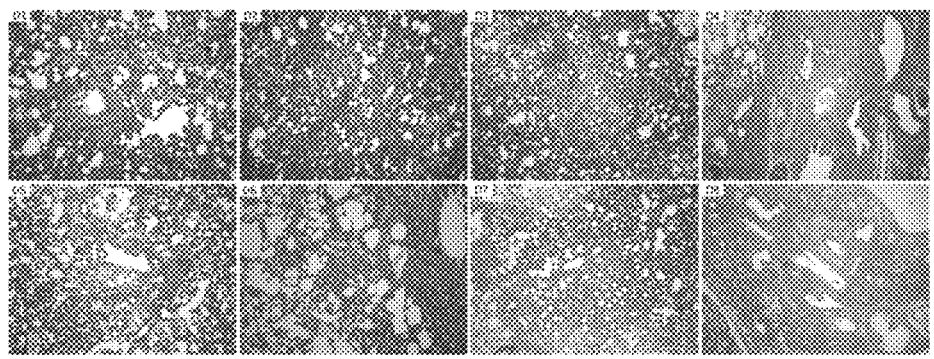

FIG. 3B: Lung tissue profiles of rats from Group D
(Saline control group) with bleomycin-induced pulmonary fibrosis (HE×100)

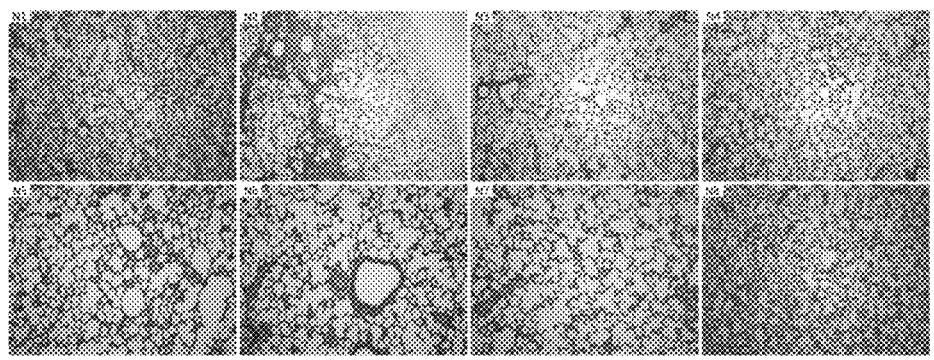

FIG. 3C: Lung tissue profiles of rats from Group N
(Normal control group) which did not receive any treating (HE×100)

BOTANICAL COMPOSITION AND METHODS OF MANUFACTURE AND USE

The present application is a continuation-in-part of and claims priority to International Application No. PCT/US2011/044488 filed Jul. 19, 2011, the entire contents of which are incorporated herein by reference.

The following specification relates to a botanical composition and combinations thereof useful at treating and/or preventing histamine-mediated conditions or disorders as well as the methods of manufacture and use thereof.

BACKGROUND

Histamine is a hydrophilic vasoactive amine, or an important messenger molecule released from activated mast cells, white blood cells called basophils, enterochromaffin-like cells, and neurons. Histamine plays a pathophysiological regulatory role in cellular events through binding to four types of histamine receptors (i.e. H1R, H2R, H3R and H4R), they being G-protein-coupled receptors with histamine as their endogenous ligand.

The various biological effects of histamine mediated through the activation of specific histamine H1, H2, H3 and H4 receptors differ in their tissue expression patterns and functions. All four types known histamine receptors (i.e. H1R, H2R, H3R, and H4R) have been used or proposed as therapeutic targets for a wide variety of diseases. Histamine H1 receptor causes systemic vasodilatation, smooth muscle contraction, separation of endothelial cells, potentiation of pain, and pruritus etc. Histamine H2 receptor is primarily involved in vasodilation and also stimulates gastric acid secretion. Histamine H3 receptor decreases neurotransmitters (e.g. histamine, etc.) release from the neurons. Histamine H4 receptor has been shown to be involved in chemotaxis and inflammatory mediators released by eosinophils, mast cells, monocytes, dendritic cells, and T cells.

Histamine receptor antagonists to block action of histamine have found use in therapy for the various diseases, such as allergic inflammatory conditions, tissue and organ fibrosis, different diseases associated with abnormal neurotransmitter levels, immune system disorders, and the conditions or disorders involved in abnormal cell proliferation including both benign and malignant tumor cells, etc.

However, conventional medicines may often cause uncertain side effects. For example, Loratadine (or Claritin, Claritin RediTabs, etc.), one of histamine H1 receptor antagonists may commonly cause headache, drowsiness, fatigue and dry mouth. In addition, major side effects of Famotidine (i.e. Pepcid, a histamine H2 receptor antagonist) include constipation, diarrhea, fatigue, headache, insomnia, muscle pain, nausea, and vomiting.

Additionally, inhaled corticosteroids are first-line agents for conventional treatment in severe acute asthma attacks mediated by histamine receptors; and the administration of corticosteroids and pharmaceutical compositions comprising corticosteroids can promote wound healing and reduce scar formation, as described in international patent application publication WO/2011/006100 Method of Wound Healing and Scar Modulation. But, long-term use of corticosteroids can have many side effects including thinning of the skin and easy bruising, a redistribution of fat, increased appetite, weight gain, blood glucose problems, insomnia, and emotional changes, etc.

Furthermore, it is known that nasal congestion or stuffy nose, one of symptoms of allergic rhinitis, is the blockage of the nasal passages usually due to membranes lining of the nose becoming swollen resulting from inflamed blood vessels. Decongestants can provide significant symptom relief of nasal congestion. Clinically, topical decongestants are generally used to apply directly to the nasal cavity to relieve nasal congestion in order to reduce the side effects associated with systemically-acting decongestants. For example, phenylephrine, the most common over-the-counter (OTC) decongestant in the United States, used as a decongestant and sold as an oral medicine, nasal spray, or eye drops, but one of side effects is high blood pressure caused by vasoconstriction.

However, topical decongestants should only be used by patients for a maximum of three days in a row because rebound congestion may occur in the form of rhinitis medicamentosa that is a condition of rebound nasal congestion brought on by extended use of topical decongestants, such as oxymetazoline, a more common nasal spray. Decongestants are normally paired with antihistamines to lessen this effect, but the combination of both classes of drugs does not necessarily cancel the side effects of each other. The common side effects of decongestants include sleeplessness, anxiety, dizziness, excitability, and nervousness besides hypertension.

Accordingly, patients may be seeking out alternative treatments to avoid the adverse effects of conventional treatments that may be invasive and expensive, and there is a need in the art for a safe and effective alternative method by which to treat and/or prevent the conditions or disorders mediated by histamine, particularly, natural products for promotion of health as well as treatment of disease.

SUMMARY

In view of the problems related to the known methods and medications used to treat conditions or disorders mediated by histamine, the present specification describes a botanical composition comprising a leaf extract of *Hylotelephium spectabile* (Boreau) *H. Ohba* (Synonym: *Sedum spectabile* Boreau or *Sedum spectabile* Bor., called "*Hylotelephium spectabile*", "*Sedum spectabile*", or "*Hylotelephium*" for short hereinafter, for the photograph, vide: http://www.zhiwutong.com/dan_tu/70/56014.htm; A leaf extract thereof called "*Hylotelephium* composition" for short hereinafter) and combinations thereof with diverse bioactive actions for a subject at risk of or suffering from the histamine-mediated conditions or disorders. Advantageously, the compositions described in the present specification are relatively inexpensive to manufacture, provide an immediate effects, safe to administer, and easy to apply.

It is also contemplated to administer a therapeutically effective amount of *Hylotelephium* composition or combinations thereof to a subject in need thereof for treating and/or preventing histamine-mediated conditions or disorders. Methods of manufacture and use thereof are also contemplated.

BRIEF DESCRIPTION OF THE DRAWINGS

FIGS. 1A and 1B show the changes of body weight of rats from the *Hylotelephium* composition treatment group where pulmonary fibrosis was induced by injecting bleomycin rats from the saline control group where pulmonary fibrosis was induced by injecting bleomycin, and rats from normal control group where the rats were not treated.

FIG. 2A shows the lung tissue profiles of typical rats obtained by the histological examinations, wherein, Normal control group (i.e. N2 and N6; HE×100): in the observed lung tissues of rats without any treating, the structures were clear, inflammatory cell infiltration did not occur, and both the airway and alveolar tissues retained their normal profiles without the widened alveolar septa; Saline control group (i.e. D4 and D8; HE×100): in the observed lung tissues of rats where pulmonary fibrosis was induced by injecting bleomycin, and severe pulmonary fibrosis occurred including pulmonary interstitial fibrosis, diffuse alveolar septa widened, alveolar structure disordered, visible alveolar locking disappeared, mild alveolitis, and bronchial epithelial hyperplasia, etc.; *Hylotelephium* composition treatment group (i.e. C1 and C6; HE×100): in the observed lung tissues of rats where pulmonary fibrosis was induced by injecting bleomycin, the said conditions observed in Saline control group were significantly improved, such as the severe fibrosis, widened alveolar septa, and the disordered alveolar structures, etc.

FIG. 2B shows the effect of *Hylotelephium* composition on hydroxyproline (HYP) content in rat's left lung tissue with fibrosis, wherein, the rats in Normal control group did not receive any treating; the rats in Saline control group where pulmonary fibrosis was induced by injecting bleomycin; the rats in *Hylotelephium* composition treatment group where pulmonary fibrosis was induced by injecting bleomycin; shows compared with Normal control group; (P<0.05); n=8.

FIG. 3A shows the lung tissue profiles of rats from. Group C (*Hylotelephium* composition treatment group; i.e. C1~C8; HE×100) with bleomycin-induced pulmonary fibrosis; FIG. 3B shows the lung tissue profiles of rats from Group D (Saline control group; i.e. D1~D8; HE×100) with bleomycin-induced pulmonary fibrosis. FIG. 3C shows the lung tissue profiles of rats from Group N (Normal control group; i.e. N1~N8; HE×100) without any treating.

DETAILED DESCRIPTION

The term "*Hylotelephium* composition" is used herein to refer to a leaf extract of *Hylotelephium spectabile* (Boreau) *H. Ohba*, and the term "extract" refers to liquid, semi-liquid, or solid preparation thereof.

The term "subject" is used herein to refer to a mammal, such as a human, pig, cattle, sheep, rabbit, horse, dog, cat, and rat, etc. Preferably the mammal is a human—e.g., an individual including infants, children, adults, the aged, or pregnant or lactating women.

*Hylotelephium* composition may be administered regularly or as needed to a subject orally, topically (e.g., eye drops, ear drops, and some forms suitable for buccal or nasal administration by inhalation, insufflations or spray of powders), or parenterally (e.g., subcutaneously, intramuscularly, intravenously, intraperitoneally, rectally, intravaginally), and the like. As discussed above, the particularly preferred route of administration is oral or topical (i.e. systemic or local).

A therapeutically effective amount can be ascertained by experiments described below, and it may be also ascertained by considering the following factors, for example, the mode or route of administration or drug delivery, severity or course of conditions, subject's previous or ongoing therapy, subject's health status and response to drugs, and the judgment given by a treating physician, etc. When topically administered, the exemplary amount is equivalent to the amount of from about 0.01 grams to about 5 grams of fresh *Hylotelephium* leaves (wet weight) per kg of subject's body weight per 24 hours, preferably equivalent to the amount of from about 0.01 grams to about 3 grams of fresh *Hylotelephium* leaves (wet weight) per kg of subject's body weight per 24 hours. When orally administered, the exemplary amount is equivalent to the amount of from about 1 grams to about 5 grams of fresh *Hylotelephium* leaves (wet weight) per kg of subject's body weight per 24 hours, preferably equivalent to the amount of from about 2 grams to about 4 grams of fresh *Hylotelephium* leaves (wet weight) per kg of subject's body weight per 24 hours.

In one embodiment, the liquid preparation of *Hylotelephium* composition may be prepared according to the following steps. Fresh *Hylotelephium* leaves are washed, cleaned by rinsing with purified water, air dried at room temperature, and then frozen below −4 degree Celsius. The frozen leaves are crushed, ground into a pulp and thawed at room temperature; the thawed leaf pulp is again frozen below −4 degree Celsius, and then the frozen leaf pulp is again thawed at room temperature; the above freezing-thawing process steps are repeated in order to break cell walls and change tissue structure of the plant; the number of successive freeze-thaw cycles ranges from zero (that is, thawing only) to six, and the particularly preferred number is three or four; the resulting leaf pulp is then separated into liquid and residual parts by appropriate methods such as filtration, or centrifugation, etc., and the liquid and the solid collected are respectively sterilized and stored at −18 degree Celsius.

The semi-liquid preparation of *Hylotelephium* composition may be prepared from the liquid preparation further evaporated or concentrated. The solid preparation of *Hylotelephium* composition may be eventually made from the semi-solid preparation or directly made from the fresh leaves of *Hylotelephium spectabile* using standard equipment known in the art, including, but not limited to, spray drying, vacuum drying, fluid-bed drying, freeze-drying (also known as lyophilization), and the like.

According to various embodiments, *Hylotelephium* composition may be administered or delivered orally, topically, or both; in the form of liquid, semi-liquid, or solid preparation; either alone or in combination with other compositions; which depend on the intended end use application.

According to one embodiment, the liquid preparation of *Hylotelephium* composition includes, but is not limited to, solutions (e.g., sterile packaged injection, eye drops, or ear drops), suspensions, suitably flavored syrups, and emulsions with edible oils such as coconut oil or similar pharmaceutical vehicles. The semi-liquid preparation of *Hylotelephium* composition includes, but is not limited to, gel, cream, paste, or plaster, etc. Both liquid and semi-liquid preparations of *Hylotelephium* composition may be used to make topically therapeutic agents, wound dressings, cosmetics aesthetically improving appearance of the skin, skin moisturizers to counter skin cracking and dryness, the medicated shampoos to help decrease itchy scalp and dandruff. Particularly, both liquid and semi-liquid preparations of *Hylotelephium* composition can act as an essential bioactive composition to make functional foods or functional beverages.

According to one embodiment, the solid preparation of *Hylotelephium* composition includes, but is not limited to, powders (e.g., sterile packaged powders for injection, nasal powder spray, buccal powder spray, inhalation powders, insufflations powders, and topical powders, etc.), tablets, effervescent tablets, chewable tablets, rapidly disintegrating tablets, pills, capsules, polymeric microcapsules or microvesicles, dispersible granules, lozenges, suppositories. The solid preparations of *Hylotelephium* composition may be used to make dietary supplements. The solid preparation for rectal or vaginal administration may be suppositories that can be prepared by mixing *Hylotelephium* composition with suitable non-irritating carriers such as polyethylene glycol or a suppository wax, which is solid at ambient temperature but liquid at body temperature in order to melt in the rectum or vaginal cavity and release the active composition.

According to one aspect, wherein *Hylotelephium* composition may be combined with a pharmaceutically acceptable excipient or carrier depending on the intended end use application. The pharmaceutically compatible and acceptable carriers or excipients known in the art include, but not limited to, diluents, medium for the active ingredient, dispersion or suspension aids, surface active agents, isotonic agents, thickening or emulsifying agents, sweetening agents, flavoring agents, coloring agents, preservatives as well as solid binders, suitable inert fillers (e.g., sodium and calcium carbonate, sodium and calcium phosphate, lactose, starch, sugar, glucose, methyl cellulose, magnesium stearate, mannitol, and sorbitol, etc.), lubricants, and the like. If desired, the tablets may be coated with a material such as glyceryl monostearate or glyceryl distearate or with an enteric coating to delay absorption in the gastrointestinal tract.

For example, according to another aspect, wherein *Hylotelephium* composition as an essentially bioactive composition may be further combined with pharmaceutically acceptable excipient or carrier for making dietary supplements in various product forms including, but not limited to, tablets, effervescent tablets, chewable tablets, rapidly disintegrating tablets, pills, capsules, or dispersible granules, etc., particularly preferred product forms are chewable tablets, effervescent tablets, or rapidly disintegrating tablets. Especially, the solid preparations of *Hylotelephium* composition can act as an essential bioactive composition to make dietary supplements in the various forms of products.

According to another aspect, wherein *Hylotelephium* composition may be combined with food compositions including, but not limited to, cocoa powders, chocolate fillings, honey, fruit juices, sweetening agents, or flavoring agents, etc. with the aim of providing functional foods or functional beverages for subjects at risk of or suffering from the said conditions, they including infants, children, adults, the aged, or pregnant or lactating women. Thereby *Hylotelephium* composition in product forms of functional foods, functional beverages, or other delicious foods can provide more options for populations with different flavor preferences or those children who hate taking medicines in view of they can be conveniently administrated to infants or children.

According to another aspect, wherein *Hylotelephium* composition may be further combined with another botanical composition as a second bioactive agent to prepare topically therapeutic agents. The botanical composition as the second bioactive agent comprises melon seed sprout juices of plants in the family Cucurbitaceae, they including, but are not limited to, watermelon, cantaloupe, and honeydew melon, etc., particularly preferred botanical composition is watermelon seed sprout juices.

The botanical components as the second bioactive agent are used in a therapeutically effective amount of from about 10% to 50% of the whole compositions by weight, and particularly preferred amount is 50%.

In the "Omnibus of Herbal Medicine in China", the muskmelon pedicle of *Cucumis melo* L. in the family Cucurbitaceae (commonly referred to as cucurbit including watermelon, muskmelon, cantaloupe and honeydew melon, etc.) is used to induce vomiting to discharge phlegm and fluid, retained food and toxic substances. When ground into powder or "Melon Pedicle Powder" for smelling, it is used for jaundice of damp heat. It has been suggested that Muskmelon pedicle contains cucurbitacin, which has been noted to have an anti-hepatitis effect and to prevent fatty liver. It can stimulate gastric mucous to induce vomiting. Moreover, the fruits of *Cucumis melo* L. can be used as a cooling light cleanser or moisturizer for the skin. They may be used as a first aid treatment for burns and abrasions (http://www.e2121.com/herb_db/viewherb.php3?viewid=624&setlang=).

The seeds of *Cucumis melo* L. (Cucurbitaceae) are used in traditional Chinese medicine as antitussive, digestive, febrifuge and vermifuge; and melon seed extract can be used as an antidiabetic and is beneficial in chronic eczema [Carmen Festaa, et al, "Phenolic Glycosides from *Cucumis melo* var. *inodorus* Seeds" International PSE Symposium on Natural Products in Cancer Therapy, 23-26 Sep. 2008, Naples, Italy, Abstracts].

However, it has been found that watermelon seed sprout juice actually has detumescence, anti-inflammatory, antibacterial, antifungal, antipruritic, and anti-hyperalgesic, etc. actions. Thereby the combination of *Hylotelephium* composition and composition of the watermelon seed sprout juice acting as topically therapeutic agents can provide complementary, synergistic, and enhancive actions for exerting the some therapeutic effects of *Hylotelephium* composition, and the said combination is called Combination-HW for short hereinafter.

Therapeutical Use of *Hylotelephium* Composition and Combinations Thereof.

Another aspect includes therapeutically use of *Hylotelephium* composition and combination thereof in a subject at risk of or suffering from the histamine-mediated conditions or disorders. The efficacy of *Hylotelephium* composition and combination thereof for treating and/or preventing histamine-mediated conditions or disorders by means of comparisons among histamine receptor antagonists and *Hylotelephium* composition and combinations thereof is described in the present specification.

Allergy is one of four forms of hypersensitivity and is called type I (or immediate) hypersensitivity allergic reactions. It is characterized by excessive activation of mast cells and basophils by the allergen binding to the IgE antibodies held on the surface of the mast cells or basophils. Mast cells and basophils will degranulate if sensitized by IgE antibodies attached to the membranes when exposed to the environmental appropriate antigen. Activated mast cells and basophils release histamine and other chemical mediators into the surrounding tissue during the degranulation. These mediators have an effect on nerve cells causing itching, smooth muscle cells causing contraction, goblet cells causing excessive mucus production, and endothelial cells causing vasodilatation and edema.

The release of histamine and activated mast cells degranulation play a crucial role in the pathogenesis of immediate allergic reaction and cause goblet cell hyperplasia resulting in excessive mucus production and secretion, while goblet cell hyperplasia is a prominent feature of chronic allergic airway inflammation such as asthma.

For example, histamine dilates post capillary venules, activates the endothelium, and increases blood vessel permeability. This leads to local edema (swelling), warmth, redness, and the attraction of other inflammatory cells to the site of histamine release. Histamine also irritates nerve endings leading to itching or pain by acting on sensory nerve terminals. Clinically, histamine H1 receptor antagonists (or H1 antihistamines) are commonly used on a regular basis, rather than as needed, to reduce effects mediated by histamine as an endogenous chemical mediator released during allergic responses and thereby to suppress various symptoms caused by allergies and Inflammation.

Oral H1 antihistamines are first-line therapy for mild-to-moderate allergic rhinitis. Some of the newer oral antihistamines, such as cetirizine, desloratadine, and fexofenadine, have been shown to relieve the symptom of nasal congestion

[Rosenwasser L J. "Treatment of allergic rhinitis" Am J Med. 2002 Dec. 16; 113 Suppl 9A: 17S-24S (Vide: http://www.ncbi.nlm.nih.gov/pubmed?term=12517578)].

It has been reported that using histamine H1, H2, H3, and H4 receptor antagonists to treat and prevent asthma and allergic inflammation. For example, United States Patent Application 2004/0127395 describes the effects of histamine H4 receptor modulators on asthma and/or allergic responses. Also, United States Patent Application 2005/0090527 describes a method for treating or preventing an allergic or non-allergic condition with characteristics of airway inflammation. It has been suggested that some combinations of various histamine receptor antagonists can be used for treating pruritus, for example, United States Patent Application 2009/0069343 describes a method of treating a subject suffering from pruritus by administering at least one histamine H1 receptor antagonist with centrally acting and at least one histamine H4 receptor antagonist to such subject.

Allergic conjunctivitis is inflammation of the conjunctiva due to allergy, and the most common cause is hay fever. Moreover, allergic rhinoconjunctivitis may occur if allergic conjunctivitis is combined with rhinitis. One treatment of allergic conjunctivitis is to avoid the allergen and to use antihistamines, either topical (in the form of eye drops) or systemic (in the form of tablets) to stabilize mast cells (http://en.wikipedia.org/wiki/Allergic_conjunctivitis).

Histamine and other pro-inflammatory substances are released from activated mast cells, basophils and other inflammatory cells in response to the binding of allergen-bound IgE antibodies to histamine receptors. Therefore, histamine is thought to play an important role, especially in a variety of skin inflammatory conditions such as ionizing radiation, eczema, urticaria (or hives), insect stings, and contact dermatitis caused by the unknown irritants in allergic or non-allergic reactions.

An investigation on ultraviolet-induced erythema reaction in four subjects provided the first evidence that histamine may mediate the early phase of the human sunburn reaction [Gilchrest B A, et al., "The human sunburn reaction: histologic and biochemical studies" J Am Acad Dermatol. 1981 October; 5(4): 411-22 (or vide: http://www.ncbi.nlm.nih.gov/pubmed/7287956)]. Another study to elucidate the mechanism of sun exposure-induced exacerbation of skin lesions in atopic dermatitis found that histamine is elevated in the skin of patients with atopic dermatitis and considered to play a pathogenic role in atopic dermatitis induced by sun exposure [Shinoda S, et al., "Histamine enhances UVB-induced IL-6 production by human keratinocytes" Arch Dermatol Res. 1998 August; 290(8): 429-34 (or vide: http://www.ncbi.nlm.nih.gov/pubmed/9763305)].

The study suggests that radiation-induced mast cells mediators have a tremendous impact on inflammatory cell recruitment into irradiated skin, and it is postulated that activation of mast cells to be an initial key event in the cutaneous radiation reaction, which might offer promising targets for treatment of both the side effects in radiation therapy and radiation injuries [Müller K, et al., "Radiation-induced mast cell mediators differentially modulate chemokine release from dermal fibroblasts" J Dermatol Sci. 2011 March; 61(3): 199-205. Epub 2011 Jan. 15 (or vide: http://www.ncbi.nlm.nih.gov/pubmed/21292447)].

Food allergies, particularly IgE mediated food allergies are classified as type-I immediate hypersensitivity, and the symptoms affect the skin, gastrointestinal tract, and in severe cases, the respiratory tract and blood circulation. It is thought that food allergens trigger an inflammatory response involving activated mast cells degranulation and recruitment of eosinophils. Food allergies are also thought to develop more easily in patients with an atopic syndrome, which is a very common combination of diseases including allergic rhinitis, allergic conjunctivitis, eczema, and asthma. The mainstay of treatment for food allergies is avoidance of the foods that have been identified as allergens, and the treatments include antihistamines, and steroids, etc. (http://en.wikipedia.org/wiki/Food_allergy).

In brief, use of histamine receptor antagonists is an established approach to block histamine effects on allergic and inflammatory conditions based on histamine has been recognized as a key factor in the pathogenesis of allergy, and inflammation, etc.

According to some embodiments, *Hylotelephium* composition and combination thereof may be administered to a subject as well, either regularly or only when needed, orally, topically, or both, for treating and/or preventing allergic inflammation, including, but are not limited to, extrinsic or intrinsic asthma, airway inflammation, respiratory disorders associated with excess airway mucus production, exercise-induced asthma, bronchitis, allergic rhinitis including seasonal and perennial allergic rhinitis, non-allergic rhinitis, nasal congestion, allergic sinusitis, rhinitis medicamentosa, drug reactions, allergic rhinoconjunctivitis, headaches, colds, allergic conjunctivitis, vernal keratoconjunctivitis, angular blepharitis, otitis media, food allergies, atopic dermatitis, eczema, atopic syndrome, insect sting allergy, inflammatory or neuropathic pain, actinic dermatitis, contact dermatitis caused by the unknown irritants in allergic or non-allergic reactions, urticaria (or hives), fixed drug eruption, urticaria pigmentosa, mastocytosis, cutaneous scars, cystic fibrosis, pulmonary fibrosis, kidney fibrosis, liver fibrosis, multiple sclerosis, neurofibrosis, chronic obstructive pulmonary disease (COPD), emphysema, pulmonary hypertension, benign tumor, malignant tumor, cherry angiomas, pigmented nevus, melanoma, rheumatoid arthritis, osteoarthritis, pruritus, pain, hyperpigmentation, seborrheic keratosis, itchy scalp, excessive dandruff, skin cracking, burn, or scald. gastrointestinal tract diseases, intestinal inflammatory diseases secondary to radiation exposure or allergen exposure, inflammatory bowel disease (e.g. Crohn's disease or ulcerative colitis), inflammation response caused by ionizing radiation, and the like.

Particularly preferred conditions treated, ameliorated, or reduced by administration of *Hylotelephium* composition and combination thereof include extrinsic or intrinsic asthma, respiratory disorders associated with excess airway mucus production, allergic rhinitis, allergic sinusitis, allergic conjunctivitis, allergic rhinoconjunctivitis, rhinitis medicamentosa, drug reactions, food allergy, atopic syndrome, gastrointestinal allergy, eczema, urticarial, cutaneous scars, cystic fibrosis, pulmonary fibrosis, kidney fibrosis, liver fibrosis, scleroderma, multiple sclerosis, neurofibrosis, chronic obstructive pulmonary disease (COPD), emphysema, pulmonary hypertension, benign tumor, malignant tumor, cherry angiomas, pigmented nevus, melanoma, pruritus, pain, hyperpigmentation, seborrheic keratosis, itchy scalp, excessive dandruff, skin cracking, burn, scald, or inflammatory response caused by ionizing radiation.

In an aspect of some embodiments, orally administering a therapeutically effective amount of *Hylotelephium* composition, only when needed, immediately relieved the various symptoms of acute asthma onsets in a subject following exposure to the appropriate allergens or irritants from air pollutants whenever occurred, including chest pain or tightness, shortness of breath, wheezing, cough, and frequent expectorating phlegm. Particularly, the inordinate production and secretion of mucus was successfully suppressed even within minutes, which demonstrated that *Hylotelephium* composition effectively suppressed goblet cell hyperplasia and thereby reduced excessive production and secretion of mucus from the airways in addition to relaxing smooth muscle contraction and reducing inflammation.

In another aspect of some embodiments, without the need to combine with a decongestant, orally administering a therapeutically effective amount of *Hylotelephium* composition (only when needed) helped a subject inhibiting the symptoms caused by allergic rhinitis (i.e. hay fever or pollenosis) including seasonal and perennial allergic rhinitis, such as a runny nose or a stuffy nose, sneezing, itchy sensation in the eyes and nose. As well, relying on the conclusive evidence accumulated in the experiments, Combination-HW (i.e. a combination of *Hylotelephium* composition and composition of watermelon seed sprout juice) in the form of nasal spray or eye drops has been proven efficacious for relief of the nasal congestion that is a typical symptom of allergic rhinitis or rhinitis medicamentosa brought on by extended use of topical decongestants. Moreover, orally administering *Hylotelephium* composition significantly reduced the risk of allergic rhinitis in the pollen season and also prevented the progression of allergic rhinitis to asthma.

In another aspect of some embodiments, the topical administration of *Hylotelephium* composition or Combination-HW in the form of eye drops efficaciously relieved the symptoms caused by allergic conjunctivitis, vernal keratoconjunctivitis, or allergic rhinoconjunctivitis, such as, severely itchy and watery eyes with foreign body sensation, ocular redness, and swelling of the conjunctiva, etc.

In another aspect of some embodiments, the topical administration of *Hylotelephium* composition or Combination-HW in the form of a skin lotion was used for treating various allergic and/or non-allergic dermatological conditions such as atopic dermatitis, urticaria (hives), sunburns, and skin inflammation caused by overexposure to direct sunlight etc. in order to reduce the symptoms of redness, itching, pain, even blistering. For instance, after Trial I (i.e. an experiment on orally administering a therapeutically effective amount of *Hylotelephium* composition every day to a subject on a regular basis for 72 consecutive days), the erythema or red spots on a subject's face decreased in size almost a half as well as the rest part distinctly faded rather than growing progressively and developing into a brown spot.

In some embodiments, Combination-HW can serve not only as the potential first aid treatment agent for acute partial-thickness scald or burn injuries to relieve pain but also as anti-pruritus agent to reduce the typical itching felt around a healing scab in addition to chronic pruritus induced by the various causes.

Particularly, in the experiments, Combination-HW exerted the diverse bioactive actions as follows: reduction of inflammation, swelling, and burning sensation in the skin; immediate relief of formication (or skin paresthesia) due to unknown cause; potent inhibition of pruritus caused by various allergic or non-allergic reactions and metabolic disorders; elimination of inflammatory, nociceptive, or neuropathic pain; treatment of angular blepharitis, insect stings, seborrheic dermatitis, sunburns, angioedema, burn, scald, skin cracking resulting from skin dryness, etc.; effective alleviation of the various symptoms resulting from atopic dermatitis, eczema, or urticaria (hives).

In experiments it has been found that *Hylotelephium* composition possesses the effects similar to some effects of histamine H2 receptor antagonist used in the treatment of acid-related gastrointestinal conditions, including peptic ulcer disease, gastroesophageal reflux disease, and dyspepsia, etc. For example, orally administering *Hylotelephium* composition inhibited the excessive production and secretion of gastric acid and reduced the symptoms of acid indigestion, heartburn, stomachache, stomach cramps, or abdominal pain.

*Hylotelephium* composition exerted the significant effects in the treatment and/or prevention of histamine-mediated allergic inflammation and gave the promise of improvement of the allergic constitution of a subject susceptible to various allergic reactions and the quality of life thereof.

As well, *Hylotelephium* composition also exhibited the potent effects on the conditions associated with abnormal cell proliferation include, but are not limited to, the abnormal proliferation of goblet cells, fibroblasts, melanocytes, keratinocytes, benign or malignant tumor cells. Particularly preferred conditions or disorders include the abnormal proliferation of goblet cells, fibroblasts, melanocytes, keratinocytes, benign tumor cells or malignant tumor cells.

Moreover, according to some investigations, mediated by the release of soluble mediators such as histamine, etc., activated mast cells have been shown to promote fibroblast proliferation. Increased numbers of mast cells have been reported during the active period of hypertrophic and keloid scar formation ["Hypertrophic Scarring and Keloids: Pathomechanisms and Current and Emerging Treatment Strategies" Mol Med. 2011 January-February; 17(1-2): 113-125 (or vide: http://www.ncbi.nlm.nih.gov/pmc/articles/PMC3022978)].

The fibroblast proliferation and deposition of extracellular matrix (or ECM, with collagen as a major ECM molecule synthesized in fibrotic lesions) may result in scar formation or fibrosis after injury or medical intervention in the affected tissues. On the other hand, the scarring is created by fibroblast proliferation, or a scar in tissue and organ of the body is the evidence of fibrosis in a reparative or reactive process. For example the various type scars resulting from hyperproliferation of the connective tissue of the skin in wound healing; radiation-induced lung injury, most commonly occurring as a result of radiation therapy administered to treat cancer, involving in early inflammatory damage (radiation pneumonitis) and later complications of chronically scarring (radiation fibrosis); cirrhosis characterized by replacement of liver tissue by fibrosis or scar tissue and regenerative nodules; Dupuytren's contracture with thickening and shortening of palmar fascia that leads to flexion deformities of the fingers caused by fibroblastic proliferation and disorderly collagen deposition; scleroderma with excess collagen made by fibroblasts in the skin or other tissue and organs; and the like. All of the said conditions can lead to the destruction of architecture and function of normal tissue and organ.

According to the recent study, both human and rat lung fibroblasts express the histamine H1 and ANG II ATI receptor subtypes and when activated, they promote proliferation, transforming growth factor β1 secretion, and collagen synthesis. Mast cells appear to be critical to pulmonary fibrosis. Therapeutic blockade of mast cell degranulation and/or histamine and ANG II receptors should attenuate pulmonary fibrosis [Veerappan A, et al., "Mast cells: a pivotal role in pulmonary fibrosis" DNA Cell Biol. 2013 April; 32(4): 206-18 (or vide: http://www.ncbi.nlm.nih.gov/pubmed/23570576)].

According to another study to explore the quantity of mast cells and the role of protease activated receptor-2 (PAR-2) in experimental rat liver fibrosis, PAR-2 mRNA expression and the protein expression of PAR-2 were consistent with the increase of the mast cells, and the content of liver hydroxyproline may play an important role in mediating liver fibrosis [Xu K S, et al., "Changes of mast cells and protease activated receptor-2 in experimental rat liver fibrosis" Zhonghua Gan Zang Bing Za Zhi. 2006 October; 14(10): 753-6 (or vide: http://www.ncbi.nlm.nih.gov/pubmed/17064469)].

According to some embodiments, in the in vivo experiments on the murine model of pulmonary fibrosis and the human subject model of cutaneous scars, *Hylotelephium* composition exhibited the above said similar actions on tissue fibrosis, exerted the bioactivities to suppress the activation of mast cells, to prevent mast cell degranulation, to reduce histamine release induced by the activated mast cells, and to inhibit fibroblast proliferation, etc. Consequently, it can be deduced that *Hylotelephium* composition is useful in a variety of tissue repair processes.

The examples indicate that *Hylotelephium* composition can potently suppress the proliferation of fibroblasts and reduce disorderly collagen deposition so that scar formation was limited. Concurrently, the outcomes in treatment of both new and old scars showed that *Hylotelephium* composition can promote the new cells to grow, while old abnormal cells can be replaced by the new cells, simultaneously exert action on degradation of disorderly extracellular matrix already deposited at a scar site, thus both new and old scars were progressively broken-down after Trial I. Excitingly, no matter how old the scar, *Hylotelephium* composition could successfully function in treatment of old scars in addition to effectually reducing formation of scar tissue (or fibrosis) and working on new scars after skin injury. Therefore, *Hylotelephium* composition can be useful for treating and/or preventing the various fibrotic diseases and various scar tissues such as hypertrophic scars, keloid scars, atrophic scars, contracture scars, and stretch marks, and the like.

Consequently, in addition to scar tissue or fibrosis resulting from hyperproliferation of the connective tissue of the skin in wound healing, *Hylotelephium* composition may hold great promise for treating and/or preventing some progressive fibroproliferative diseases that can lead to the destruction of architecture and function of normal tissue and organ, such as radiation-induced lung injury, liver cirrhosis, kidney fibrosis, Dupuytren's contracture, and multiple sclerosis, etc., where functional tissue is replaced with scar tissue after injury or medical intervention in the affected tissues. In particular, *Hylotelephium* composition can be useful at treating and/or preventing and treating radiation-induced lung injury with early inflammatory damage (radiation pneumonitis) and later complications of chronically scarring (radiation fibrosis) resulting from radiation therapy administered to treat cancer.

Hyperpigmentation is associated with hyperplasia of melanocytes [Stulberg D L, et al, "Common hyperpigmentation disorders in adults: Part II. Melanoma, seborrheic keratoses, acanthosis nigricans, melasma, diabetic dermopathy, tinea versicolor, and postinflammatory hyperpigmentation." Am Fam Physician. 2003 Nov. 15; 68(10): 1963-8 (or see: http://www.ncbi.nlm.nih.gov/pubmed/14655805)]. According to an investigation from Korea, histamine exerted a more significant effect on melanocyte proliferation than on melanogenesis, and histamine stimulated the proliferation and migration of melanocytes [Kim N H, et al, "Histamine effect on melanocyte proliferation and vitiliginous keratinocyte survival" Exp Dermatol. 2010 December; 19(12):1073-9 (or See: http://www.ncbi.nlm.nih.gov/pubmed/21054556)].

Moreover, is has been postulated that histamine is involved in ultraviolet B-induced pigmentation and that famotidine suppressed the pigmentation by the prevention of histamine binding to H2 receptors in melanocytes but not by prevention of ultraviolet B permeability and inflammation [Yoshida M, et al, "Histamine is involved in ultraviolet B-induced pigmentation of guinea pig skin" J Invest Dermatol. 2002 February; 118(2):255-60 (or see: http://www.ncbi.nlm.nih.gov/pubmed/11841541)].

The excessive accumulations of melanin produced by melanocytes or its abnormal distribution found in the epidermis or both in the epidermis and the dermis can lead to various hyperpigmentation conditions, such as hyperpigmentation scars and postinflammatory hyperpigmentation caused by skin aging (e.g. age spots) and various skin inflammatory conditions like sunburns, acne, rashes, and trauma, etc.

*Hylotelephium* composition improved the skin appearance of a subject, compared to the baseline, and the substantial changes continued during a few months after Trial I, which showed that *Hylotelephium* composition may exert action in prevention and treatment of hyperpigmentation conditions.

Histamine has been demonstrated to be involved in cell proliferation, embryonic development, and tumour growth. These various biological effects are mediated through the activation of specific histamine receptors (H1, H2, H3, and H4) that differ in their tissue expression patterns and functions. Researchers from Spain reported their recent observations of the anti-tumor effect of H1 histamine antagonists on experimental and human melanomas, and the results indicated HR1 antagonists terfenadine-treatment in vitro induced melanoma cell death by apoptosis and in vivo terfenadine treatment significantly inhibited tumor growth in murine models [Blaya B, et al, "Histamine and histamine receptor antagonists in cancer biology" Inflamm Allergy Drug Targets. 2010 Jul. 1; 9(3):146-57 (or see: http://www.ncbi.nlm.nih.gov/pubmed/20632959)].

In addition, the research results from Japan indicated that both endogenous and exogenous histamine have ability to stimulate growth of malignant melanoma implants via H2 receptors expressed in host cells [Tomita K, et al, "Histamine regulates growth of malignant melanoma implants via H2 receptors in mice" Inflammopharmacology. 2005; 13(1-3): 28'-9 (or see: http://www.ncbi.nlm.nih.gov/pubmed/16259747)].

The melanocytes begin to grow out of control, and the earliest stage of melanoma starts. Melanoma, a malignant tumor of melanocytes, is caused by frequent exposure to ultraviolet radiation present in both sun rays and emitted by artificial light sources as solariums used for tanning. The Caucasians living in sunny climates having high rates of incidence in Australia, New Zealand, North America, and northern Europe (http://en.wikipedia.org/wiki/Melanoma).

In certain embodiments, the potential effect of *Hylotelephium* composition in prevention and treatment of the conditions associated with abnormal proliferation of melanocytes and benign tumor cells is established. Moreover, *Hylotelephium* composition most possibly possesses antitumor effect and may provide an adjuvant therapy for benign and malignant tumors, such as malignant tumor melanoma, to prevent carcinogenesis in the populations at high risk of melanoma caused by ultraviolet (UV) radiation as well as preventing tumorigenesis.

In addition, dandruff can be considered aesthetically displeasing and often causes itching. It has been well established that keratinocytes play a key role in the expression and generation of immunological reactions during dandruff formation. And the pathogenesis of dandruff involves hyperproliferation of keratinocytes, resulting in deregulation of keratinization (http://en.wikipedia.org/wiki/Dandruff).

In one embodiment, *Hylotelephium* composition helped resolve the problem of itchy scalp and excessive dandruff, by which a subject was being bothered before Trial I. However, it was noticed that both itchy scalp and excessive dandruff were effectively controlled during Trial I and even 3~4 months after Trial I. It showed that *Hylotelephium* composition may work to reduce excessive dandruff and itchy scalp via suppressing abnormal proliferation of keratinocytes as well as its anti-inflammatory and antipruritic effects.

In Vivo Experiment on Murine Model of Pulmonary Fibrosis

Materials

Reagent: Bleomycin Hydrochloride for Injection made by Nippon Kayaku Co., Ltd., and Batch Number: 20121113

Experimental Animals: The twenty-four male Sprague Dawley rats of SPF grade, weighing 170 g±25 g; purchased from Laboratory Animal Center of The Academy of Military Medical Sciences, License Number: SCXK-(Army)-2002-001, Animal Certificate Number: 0009706; housed in SPF barrier environment; the use of feed, bedding and drinking water up to cleanliness standard; all experimental procedures performing the regulation of operation set up by the Laboratory Animal Center.

Methods

Preparation of bleomycin solution: The 10 mg bleomycin was dissolved in saline of 2 ml, mixed, and prepared the bleomycin solution at a concentration of 5 mg/ml.

Establishment of rat models of pulmonary fibrosis: The 24 healthy male Sprague Dawley rats were randomly divided into three groups (n=8) as *Hylotelephium* composition treatment group (Group C), saline control group (Group D), and normal control group (Group N), then 16 rats of Group C and Group D were induced to pulmonary fibrosis via slow injecting the bleomycin solution of 0.2 ml at the rat's trachea with the syringe of 1 ml.

Administration of the composition: From the second day to Day 21, *Hylotelephium* composition of 2.5 ml at the saline concentration of 0.5 g/ml in a dose of 12.5 g/kg/d was orally administered to Group C once daily, simultaneously, the same volume of saline instead of *Hylotelephium* composition was orally administered to Group D, and any composition was not administered to Group N.

Measurements: Measured the body weight of the rats in each group, observed, and recorded the general status of the rats twice weekly in the course of administration from the said second day to Day 21.

Detection of hydroxyproline (HYP) content: In order to detect hydroxyproline (HYP) levels in the serum, all the rats were sacrificed within 24 hours on Day 21, the serum was separated, and hydroxyproline (Hyp) content in the serum were detected by the ELISA kit.

Histological examination: The rats were sacrificed, the left lung tissue of the rats from each group were obtained, fixed with the 10% formalin, embedded in the dehydrated paraffin, stained by using hematoxylin-eosin staining, and histologically examined using the optical microscope.

Results

Observation of general status and statistics of body weight of the rats.

Without the abnormal mortality from the experiments, for the details of the changes of body weight of rats from each group, vide: TABLE 1 and FIG. 1A-1B.

TABLE 1 The affection of *Hylotelephium* composition on body weight of the rats with pulmonary fibrosis Group Weight (g) weight gain (g) *Hylotelephium* composition treatment group 374.94±22.63#180.75±21.94#Saline control group 381.94±10.80#182.13±17.34#Normal control group 421.19±19.01 222.63±20.07 #: Compared with the normal group, p<0.05; n=8.

FIG. 1-A and FIG. 1-B show the changes of body weight of rats, wherein Group C shows *Hylotelephium* composition treatment group from which the rats were induced the pulmonary fibrosis by injecting bleomycin; Group D shows Saline control group from which the rats were induced the pulmonary fibrosis by injecting bleomycin; Group N shows Normal control group from which the rats did not receive any treating; # shows Compared with normal control group (Group N), (P<0.05); n=8.

The results for hydroxyproline (HYP) content detected by the ELISA kit revealed that the levels of hydroxyproline content in the left lung tissue of the rats from the saline control group (Group D) was significantly greater than that of the rats from the normal control group (Group N), (P<0.05) and that the levels of hydroxyproline content in the left lung tissue of the rats from *Hylotelephium* composition treatment group (Group C) was significantly lower than that of the rats from saline control group (Group D), (P<0.05); n=8. For the details with regard to the effect of *Hylotelephium* composition on hydroxyproline (HYP) content in rat's left lung tissue with fibrosis, vide: TABLE 2 and FIG. 2.

Table 2 Effect of *Hylotelephium* composition on hydroxyproline content in rats' lung tissue with fibrosis Group HPY (ng/ml) *Hylotelephium* composition treatment group 522.35±116.59 #*Saline control group 819.95±247.67 #Normal control group 301.47±98.23 HYP: Hydroxyproline #: Compared with normal control group (Group N), (P<0.05)*: Compared with Saline control group (Group D), (P<0.05) n=8.

FIG. 2 show the effect of *Hylotelephium* composition on hydroxyproline content in rat's left lung tissue with fibrosis, wherein HYP shows Hydroxyproline; Group C shows *Hylotelephium* composition treatment group; Group D shows Saline control group; Group N shows Normal control group; # shows Compared with normal control group (Group N), (P<0.05); n=8.

The histological examination revealed:

(i) In the observed lung tissues of rats from the normal control group (Group N), the lung tissue structure of rats was clear, inflammatory cell infiltration did not occur, and both the airway and alveolar tissue retained their normal profiles without the widened alveolar septa; the lung tissue profiles of rats without any treating from normal control group (HE×100) as shown in FIG. 3C, wherein the rats from the normal control group (N1-N8) did not receive any treating.

(ii) In the observed lung tissues of rats from the saline control group (Group D), the severe pulmonary fibrosis were observed, including pulmonary interstitial fibrosis, diffuse alveolar septa widened, alveolar structure disordered, visible alveolar locking disappeared, mild alveolitis, and bronchial epithelial hyperplasia, etc.; the lung tissue injury profiles of rats with pulmonary fibrosis from saline control group (HE× 100) as shown in FIG. 3B, wherein the rats from saline control group (D1-D8) were induced the pulmonary fibrosis by injecting bleomycin.

(iii) In the observed lung tissues of rats from *Hylotelephium* composition treatment group (Group C), the conditions observed in Group D were significantly improved, such as the severe fibrosis, widened alveolar septa, and the disordered alveolar structures, etc., which exhibited the potent anti-fibrotic function of *Hylotelephium* composition; the effect of *Hylotelephium* composition on lung tissue injury of rats with pulmonary fibrosis (HE×100) as shown in FIG. 3A, wherein the rats from *Hylotelephium* composition treatment group (C1-C8) were induced the pulmonary fibrosis by injecting bleomycin.

In Vivo Experiments on Human Subject Models of Various Conditions

During the last ten years, the in vivo experiments on human subject models of a range of conditions have shown that

*Hylotelephium* composition and combinations thereof produced the reproducible uniform therapeutic outcomes without exception. The three human subjects participating in the said experiments included a healthy teen-age boy, a healthy aged man, and an aged woman who is extremely sensitive to many environmental stimuli with the case history of smallpox, childhood bronchial asthma, penicillin anaphylactoid shock, a cesarean section, an resecting operation of the angioma in the dermis of her left hand, a suturing operation of an excessive bleeding wound on her head due to the accident in an emergency department, and scald, etc. Relying on the conclusive evidence for the significant efficacy of *Hylotelephium* composition and combinations thereof accumulated in some in vivo experiments on human subject models of a range of conditions and some therapeutic outcomes, certain aspects are embodied and illustrated in the specification. The following examples are given only for the purpose of illustration and not intended to limit the scope of the present invention.

EXPERIMENTAL EXAMPLES

Example 1

A woman experienced the onsets of acute asthma whenever she was exposed to the appropriate allergens or irritants from air pollutants, certain foods, or irritations due to unknown cause, which include cigarette smoke at high concentrations, smoke and gases from coals or woods burning, odors of sprayed insecticide or chemical agents, cooking odors of frying chili pepper, or eating less fresh shellfish, excessively salty foods, or pungent foods, etc. She first considered immediately oral administration of *Hylotelephium* composition once asthma onset occurred during the last ten years; the various symptoms such as chest pain, shortness of breath, and cough with a large amount of mucus secretion leading to frequent expectoration were Immediately relieved after the administration, particularly, the symptom of excessive mucus production was quickly inhibited even within minutes without exception.

Example 2

Concurrently, the woman was frequently bothered by perennial allergic rhinitis, allergic conjunctivitis, or allergic rhinoconjunctivitis, especially in the morning in pollen season. The symptoms were significantly suppressed provided *Hylotelephium* composition was orally administered only one time in the morning without the need to combine with any decongestant, which include sneezing, itchy nose and eyes, runny nose and/or stuffy nose, and watery and red eyes with foreign body sensation, etc. If the symptom of severe nasal congestion concurrently occurred, along with oral administration, the topical administration of *Hylotelephium* composition or Combination-HW (in the form of eye drops or nasal sprays) very quickly eliminated the symptoms such as nasal congestion, severely itchy and watery eyes with foreign body sensation, ocular redness, and swelling of the conjunctiva, etc. only within minutes.

Example 3

During the decades before the woman regularly administered *Hylotelephium* composition once daily for 72 days (called "Trial I" for short), she always experienced the acute onsets of stomachache whenever she ate crabmeat or cold foods or stomach cramps due to eating dried small shrimps; in addition, the symptoms of indigestion and excessive gastric acid secretion always occurred whenever she ate various beans, bean products, leek, potato, or sweet potato, etc. However, the above said symptoms did not occur again, and she has been being able to eat all of the said foods without scruple after Trial I.

Example 4

The woman often experienced the drug-induced allergic skin reactions to a cream containing sulfanilamide component or certain skin moisturizers with unknown components, for instance, the symptoms of redness, popular rash, itching, burning, and swelling appeared on her face in addition to burning and swelling of itchy auricles. Either oral or topical (or both) administration of *Hylotelephium* composition or topical administration of Combination-HW always effectively eliminated the said symptoms without delay.

Example 5

Moreover, Combination-HW always provided the immediate relief of formication (or skin paresthesia) on her skin due to unknown cause.

Example 6

The woman sometimes experienced pressure-induced urticaria, for instance, some itchy red blotches appeared on her buttocks after sitting for a few hours or on her loins when her loins were tightly girded up by a belt. Moreover, her hands swelled after a heavy work, and her feet swelled after walked for a long distance. The either oral or topical administration of *Hylotelephium* composition or topical administration of Combination-HW always effectively relieved the said symptoms.

Example 7

The boy participating in the in vivo experiments experienced an eczematous lesion (i.e. severe scrotum eczema) when he was busy with his entrance examination at the end of junior middle school at the age of 16 in 2004, for instance, many red papules appeared on his scrotum in addition to intense itching and redness. Unexpectedly, topical administration of *Hylotelephium* composition actually successfully cured such condition only within about 3~4 days with no later reoccurrence.

Example 8

The aged man participating in the in vivo experiments experienced an acute onset of severe dermatitis due to unknown reason with the symptoms of intense itching, red macular rashes that blends together, swelling, and oozing on large area skin of his shanks in addition to the crusted wound resulting from continuously scratching and rubbing. The topical administration of *Hylotelephium* composition effectively relieved the symptoms of itching and oozing, subside swelling, and alleviate pain in the wounds, and the rashes disappeared in a few days without symptoms reoccurrence later.

Example 9

The three subjects participating in the in vivo experiments often experienced mosquito bites in every summer. Usually, the topical administration of *Hylotelephium* composition immediately eliminated the symptoms of itching, redness and swelling. However, it was found that sometimes such administration appeared less effective and that topical administration of watermelon seed sprout juice actually eliminated the said symptoms very effectively without delay, which led to the development of Combination-HW (i.e. the combination of *Hylotelephium* composition and composition of the watermelon seed sprout juice) as a topically therapeutic agent in the forms of eye drops, nasal sprays, and skin lotion for treating and/or preventing certain histamine-mediated or non-histamine-mediated conditions, especially, used in the conditions in which *Hylotelephium* composition alone was less effective, such as, certain non-allergic dermatological conditions in addition to eczema, urticarial, or skin inflammation due to unknown reason.

Example 10

The said boy was often bothered by seborrheic dermatitis with the symptoms of redness and itching occurred around the folds of the nose and the eyebrow areas, etc. The topical administration of Combination-HW always efficaciously eliminated the said symptoms without delay.

Example 11

In order to study the feasibility of an idea, the woman suffered from an angular blepharitis that is characterized by a range of symptoms such as redness, pain and intense Itching of canthi, i.e. corners of the eye, with some irritating discharges, and even erosion in the skin around the canthi when it is severe. Fortunately, the topical administration of Combination-HW immediately relieved the said symptoms under the circumstances of *Hylotelephium* composition alone with less effective.

Example 12

The head of the woman was bumped and sutured in an emergency department because of an accident in the year before Trial I, and the result was a scar more than 1×1 cm in size left in the top of the head. It was unexpectedly founded that the scar has completely disappeared, and the hair have been healthily growing on the area bumped and sutured though Trial I had been terminated 3 months ago.

Example 13

After Trial I, four suture mark scars on the skin of woman's left hand have partially disappeared, which were produced by the resecting operation of the angioma in the dermis of her left hand 12 years ago.

Example 14

On the skin of the woman, old excessive scars were left by improper suturing during a cesarean section 22 years ago. At that time, the scars were further worsened by the scar inflammation diet (e.g. red meat and shellfish to increase arachidonic acid leading to raised inflammation levels), and it made the scars already developed into one hypertrophic scar at the site of the vertical incision and twenty suture mark scars like rolling scars (or spoon-shaped scars). It is encouraging that the old scars were gradually broken-down after Trial I, such as, the hypertrophic scar was progressively softening, flattening out, and fading; the sunken recesses of suture mark scars like rolling scars appeared partially already lifted, and then suture mark scars have been also partly smoothed out when compared to the baseline, with a few fresh hair follicles growing at the scars.

Example 15

The old hyperpigmentation scars on the skin of the woman resulting from a scald burn in childhood and new hyperpigmentation scars due to trauma have gradually faded, and even some have disappeared after Trial I. Likewise, numerous age spots or senile freckles have progressively decreased in size and faded. Also new age spots (i.e. erythema or red spots) on the woman's face appeared to decrease in size almost by one-half as well as the rest of the part was distinctly faded rather than continuing to grow and developing into brown spot (i.e. age spot) like previously.

Example 16

Most unexpectedly, even some of the most stubborn pigmented moles (i.e. nevocytic nevi, the benign tumors composed of nevus cells that are derived from melanocytes) appeared to decrease in size regardless of hereditary, innate, new growing, or their location on the body after Trial I. Interestingly, one flesh-colored intradermal nevus with the form of raised half-bulb inherited from the mother of the subject appeared to decrease in size by about one third. Likewise, a fresh grayish blue flat junctional nevus in the skin of the woman's left thumb appeared to decrease in size almost one third by compared to the baseline.

Example 17

A few nevocytic nests have disappeared, which locate within the definite sites in the purplish-bluish-black junctional nevus on left abdomen skin of the woman after Trial I.

Example 18

Concurrently, after Trial I, among two dozen red moles (also known as "cherry angiomas" or "senile angiomas") on the skin of the woman, all of them appeared to gradually flatten, some seemed to have been destroyed or decreased in duration. For instance, one red mole almost 2 mm in diameter partially faded into flesh-colored, and several tiny red moles about 1 mm in diameter seemed to be destroyed and progressively disappeared.

Example 19

Additionally, after Trial I one round waxy flat seborrheic keratose on the woman's left forearm and one rectangle-like seborrheic keratose with crusted surface on the left leg appeared to decrease in size and fade from dark brown into light tan, seborrheic keratose also known as senile keratose, a benign form of skin tumor localized hyperplastic hyperpigmented lesion being the condition commonly appearing after age 40. It is noteworthy that one new round red seborrheic keratose almost 4 cm in diameter with soft crusted surface on the left leg actually disappeared and only left a blurred trace on its site.

Example 20

The woman was also often bothered by cracked skin of her hands resulting from excessively dry skin, and the topical administration of Combination-HW effectively reduced pain and promoted healing of the skin cracks.

Example 21

The topical administration of Combination-HW helped the woman successfully curing the left hand scalded by just boiled water at the temperature about 203° F. (i.e. 95° C.), after only 20 minutes duration of administration, there was no trace of scalding on the previously scalded skin without the sensation of pain after administrating the Combination-HW.

Example 22

The topical administration of Combination-HW also helped the woman curing a right hand scalded by half a pot of just-cooked rice gruel at temperature about 194° F. (i.e. 90° F.), and it was noticed that 20 minutes after administration of the Combination-HW, the tiny trace as scalding did not exist on the most scalded skins thoroughly swabbed with Combination-HW without delay. In contrast, in those small areas where the scalded skin was not swabbed with the Combination-HW composition, the symptoms of pain, redness, swelling and blisters occurred. Moreover, it is contemplated that treatment with Combination-HW would be satisfactory if the thick gruel on the scalded skin was washed away by running water and then the scalded area swabbed with Combination-HW. Alternatively, it is believed that treatment with Combination-HW would be efficacious if the scalded hand was immediately immersed in a lotion made from Combination-HW after irrigating with running water. Moreover, after removing the fluid within blisters, the continuous administration of Combination-HW effectively relieved the symptoms of pain, redness and swelling of the scalded skin.

To sum up, all aforementioned various evidence accumulated in the experiments made with *Hylotelephium* composition and combinations thereof have demonstrated the excellent safety and effectiveness of *Hylotelephium* composition and combinations thereof for treating and/or preventing histamine-mediated or non-histamine-mediated conditions or disorders. Additionally, *Hylotelephium* composition and combinations thereof as well as the use methods of the various compositions according to the invention offer a potential new convenient way for consumers to receive multiple healthy benefits without significant down-time or other side effects.

The foregoing detailed description and accompanying examples are merely illustrative and are not to be taken as limitations upon the scope of the invention, the various changes and modifications to the embodiments wherein chosen for purposes of illustration will readily occur to those skilled in the art. To the extent that such modifications and variations do not depart from the spirit of the invention, they are intended to be included within the scope thereof.

The invention claimed is:

1. A method for treating a lung disease or disorder in a mammal in need thereof comprising systemically administering a therapeutically effective amount of a botanical composition comprising a leaf extract of *Hylotelephium spectabile* to said mammal, wherein the lung disease or disorder is selected from the group consisting of chronic obstructive pulmonary disease, pulmonary hypertension, emphysema, interstitial lung disease caused by drugs, interstitial lung disease caused by dust, pulmonary fibrosis, idiopathic pulmonary fibrosis, and cystic fibrosis.

2. The method of claim 1, wherein the lung disease or disorder is chronic obstructive pulmonary disease (COPD).

3. The method of claim 1, wherein the lung disease or disorder is pulmonary hypertension.

4. The method of claim 1, wherein the lung disease or disorder is emphysema.

5. The method of claim 1, wherein the lung disease or disorder is interstitial lung disease caused by drugs.

6. The method of claim 1, wherein the lung disease or disorder is interstitial lung disease caused by dust.

7. The method of claim 1, wherein the lung disease or disorder is pulmonary fibrosis.

8. The method of claim 1, wherein the lung disease or disorder is idiopathic pulmonary fibrosis.

9. The method of claim 1, wherein the lung disease or disorder is cystic fibrosis.

10. The method of claim 1, wherein systemically administering comprises orally administering.

* * * * *